(12) United States Patent
Mitsuhashi et al.

(10) Patent No.: US 8,622,892 B2
(45) Date of Patent: Jan. 7, 2014

(54) IN-VIVO IMAGE ACQUIRING APPARATUS AND IN-VIVO IMAGE ACQUIRING SYSTEM

(75) Inventors: Kei Mitsuhashi, Tokyo (JP); Ayako Nagase, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 1185 days.

(21) Appl. No.: 12/200,275

(22) Filed: Aug. 28, 2008

(65) Prior Publication Data

US 2009/0076326 A1   Mar. 19, 2009

(30) Foreign Application Priority Data

Aug. 29, 2007   (JP) ................. 2007-223134

(51) Int. Cl.
*A61B 1/00*    (2006.01)
*A61B 1/04*    (2006.01)

(52) U.S. Cl.
USPC .......................................... 600/118; 600/117

(58) Field of Classification Search
USPC .......................... 600/103, 109, 117–118, 160
See application file for complete search history.

(56) References Cited

U.S. PATENT DOCUMENTS

| | | |
|---|---|---|
| 2006/0155174 A1 | 7/2006 | Glukhovsky et al. |
| 2007/0185382 A1 | 8/2007 | Shimizu et al. |
| 2007/0225560 A1* | 9/2007 | Avni et al. ............ 600/118 |
| 2007/0292011 A1* | 12/2007 | Nishimura et al. ......... 382/128 |
| 2008/0177136 A1* | 7/2008 | Wang ..................... 600/109 |
| 2008/0312501 A1* | 12/2008 | Hasegawa et al. ......... 600/117 |

FOREIGN PATENT DOCUMENTS

| | | |
|---|---|---|
| JP | 2933164 | 5/1999 |
| JP | 2003-70728 | 3/2003 |
| JP | 2004-261240 A | 9/2004 |
| JP | 2005-081005 | 3/2005 |
| JP | 2005-237460 | 9/2005 |
| JP | 2006-509574 | 3/2006 |
| JP | 2007-21039 | 2/2007 |
| WO | WO 2004/096024 A1 | 3/2006 |

OTHER PUBLICATIONS

Japanese Office Action dated Jul. 17, 2012 from corresponding Japanese Patent Application No. 2007-223134 together with partial English language translation.
English language only of Japanese Patent Application Publication No. 02-031738.

* cited by examiner

*Primary Examiner* — Philip R Smith
(74) *Attorney, Agent, or Firm* — Scully, Scott, Murphy & Presser, P.C.

(57) ABSTRACT

The in-vivo image acquiring apparatus includes an imaging unit which captures an inside of a subject, a transmission processing unit which wirelessly transmits the image information captured by the imaging unit, a power supply unit which supplies driving power for each unit of the apparatus, and a switching unit which detects an external input and switches a supply state of the driving power from the power supply unit. The apparatus also includes a mode setting unit which sets predetermined operation modes based on information of the external input which is input to the switching unit, and a control unit which controls the operation of each unit of the apparatus according to the operation mode set by the mode setting unit.

9 Claims, 13 Drawing Sheets

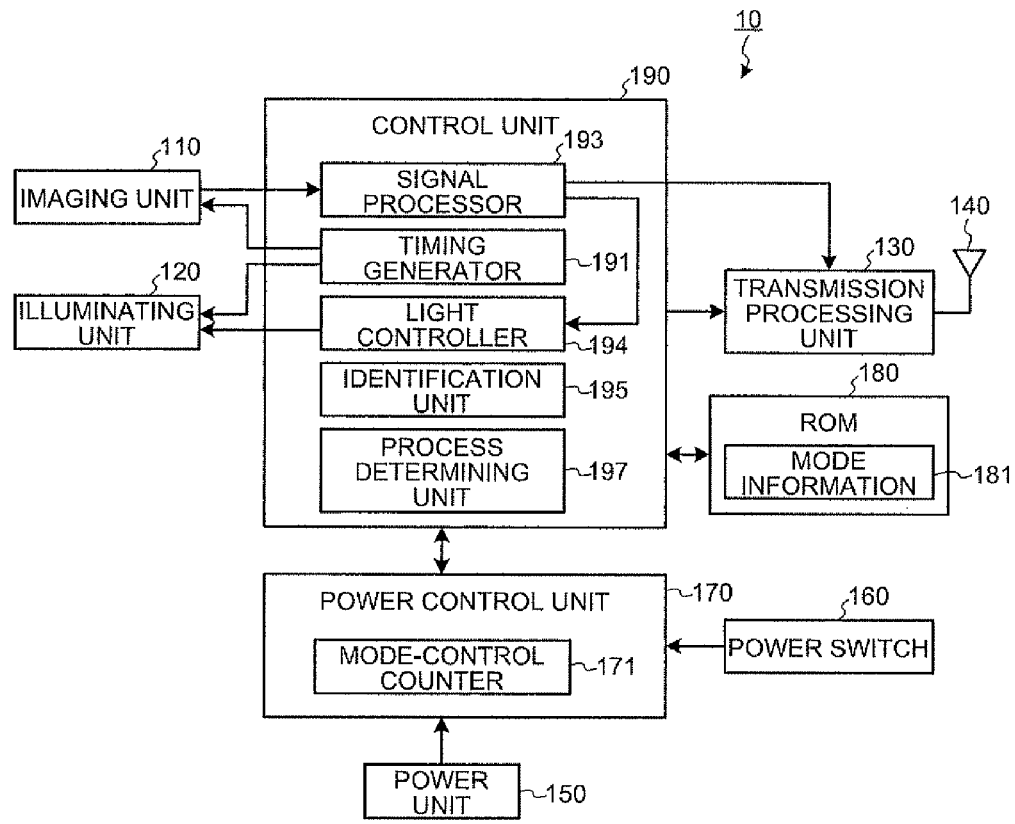

IN-VIVO IMAGE ACQUIRING APPARATUS AND IN-VIVO IMAGE ACQUIRING SYSTEM

CROSS-REFERENCE TO RELATED APPLICATIONS

This application is based upon and claims the benefit of priority from Japanese Patent Application No. 2007-223134, filed Aug. 29, 2007, the entire contents of which are incorporated herein by reference.

BACKGROUND OF THE INVENTION

1. Field of the Invention

The present invention relates to an in-vivo image acquiring apparatus which is introduced inside a subject to acquire image information of an inside of the subject, and an in-vivo image acquiring system.

2. Description of the Related Art

Recently, a swallowable capsule endoscope has been proposed in a field of endoscope. The capsule endoscope contains an imaging unit which acquires image information of an inside of a subject, an illumination unit which illuminates a portion captured by the imaging unit, a transmission unit which wirelessly transmits the image information captured by the imaging unit, and the like inside a capsule-shaped casing. The capsule endoscope is swallowed from a mouth of the subject, i.e., a patient, and introduced inside the subject. The capsule endoscope sequentially captures images inside a body cavity moving inside the body cavity with peristalsis, and wirelessly transmits the acquired image information to an outside of the body until naturally excreted.

Sometimes, an operation mode of the capsule endoscope which is introduced inside the subject needs to be changed. For example, a frame rate of the imaging may need to be changed, or a compression rate in transmission may need to be changed, depending on the imaged portion. As a technology developed to solve such problems, there is a known technology with which a position of the capsule endoscope is detected so as to change the frame rate when the capsule endoscope is at a portion such as an esophagus where the capsule endoscope passes in a short time, or when the capsule endoscope moves close around a legion or the like (see Japanese Patent Application Laid-Open No. 2003-70728). Further, in another known technology, an in-vivo state is detected by a state detector which detects an in-vivo state to change the mode (see Japanese translation of PCT international application No. 2006-509574). Further, in still another known technology, an operation-mode-change request switch is arranged, and the mode is changed by switching the switch to thereby change the frame rate and the like (see Japanese Patent Application Laid-Open No. 2007-21039). In still another known technology, a receiving device which receives an operation-command signal from an outside is attached to the capsule endoscope, and a measuring operation is performed according to the operation command signal received by the receiving device (see Japanese Patent No. 2933164).

SUMMARY OF THE INVENTION

An in-vivo image acquiring apparatus according to an aspect of the present invention is introduced inside a subject, captures an inside of the subject, and outputs acquired image information to an outside. The in-vivo image acquiring apparatus includes an imaging unit that captures the inside of the subject, a transmission processing unit that performs a process that wirelessly transmits the image information captured by the imaging unit, a power supplying unit that supplies driving power for each unit of the apparatus, a switching unit that detects an external input and switches a supply state of the driving power supplied by the power supplying unit, a mode setting unit that sets a predetermined operation mode based on information of the external input that is input to the switching unit, and a control unit that controls an operation of each unit of the apparatus according to the operation mode set by the mode setting unit.

An in-vivo image acquiring system according to another aspect of the present invention includes an in-vivo image acquiring apparatus that is introduced inside a subject to capture an inside of the subject and to output acquired image information to an outside, and that includes an imaging unit that captures the inside of the subject, a transmission processing unit that performs a process that wirelessly transmits the image information captured by the imaging unit, a power supplying unit that supplies driving power for each unit of the apparatus, a switching unit that detects an external input and switches a supply state of the driving power supplied by the power supplying unit, a mode setting unit that sets a predetermined operation mode based on information of the external input that is input to the switching unit, and a control unit that controls an operation of each unit of the apparatus according to the operation mode set by the mode setting unit, a receiving unit that is arranged outside of the subject and receives image information which is wirelessly transmitted from the in-vivo image acquiring apparatus information of the operation mode on which the image information is captured, and a display processing unit that performs a process that displays the image information received by the receiving unit and the received operation-mode information on a display unit.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a block diagram of a functional configuration of the capsule endoscope according to the first embodiment;

FIG. 4 is a diagram showing an example of an operation mode of the capsule endoscope and a control content thereof;

DETAILED DESCRIPTION OF THE PREFERRED EMBODIMENTS

Exemplary embodiments of the present invention are described in detail below with reference to the accompanying drawings.

Figure 1:
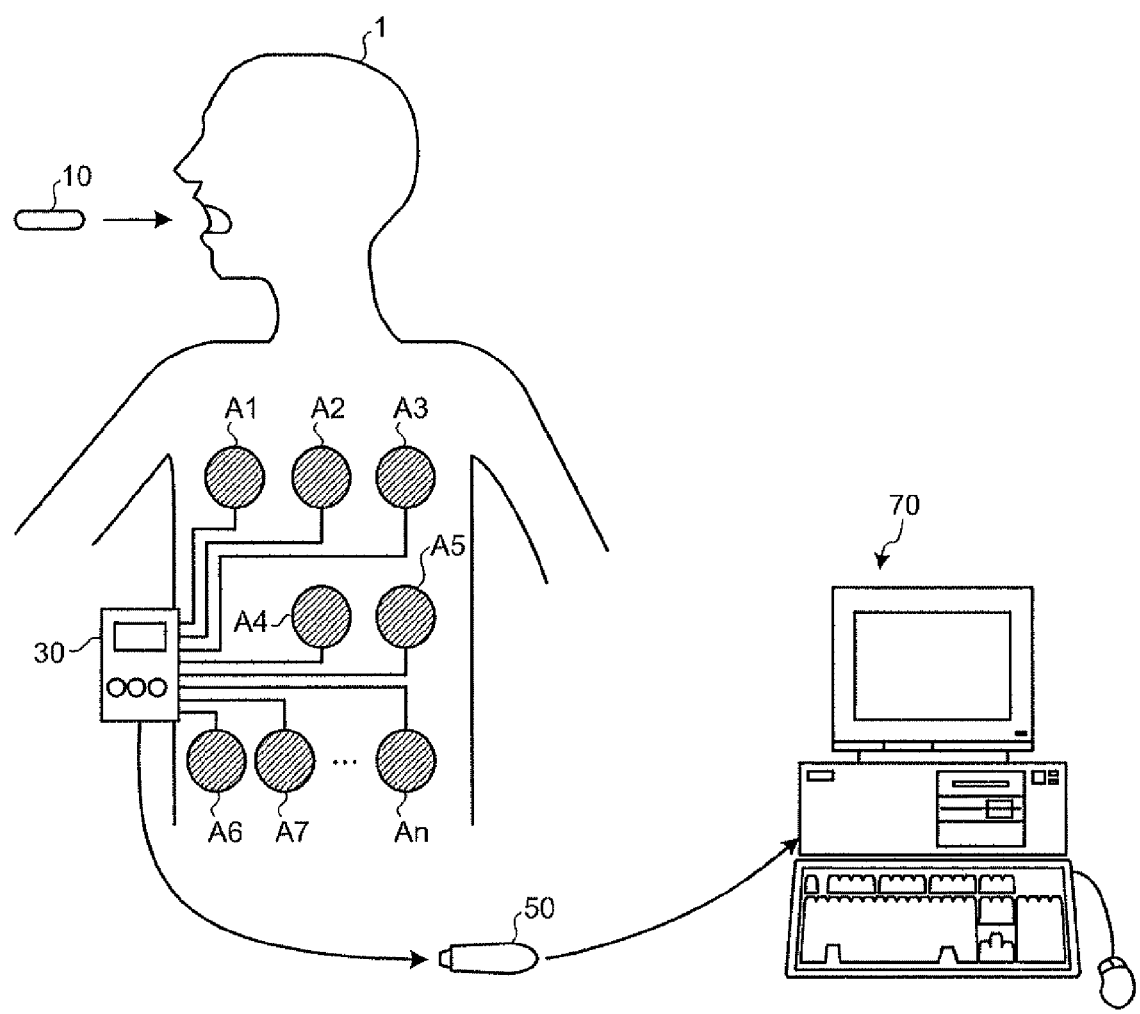
FIG. 1 is a schematic diagram of an overall configuration of an in-vivo image acquiring system according to a first embodiment.

FIG. 1 is a schematic diagram of an overall configuration of an in-vivo image acquiring system according to a first embodiment. As shown in FIG. 1, the in-vivo image acquiring system includes a capsule endoscope 10, a receiving device 30, and a display device 70. The capsule endoscope 10, i.e., an in-vivo image acquiring apparatus acquires image information inside a subject 1. The receiving device 30 receives image information wirelessly transmitted from the capsule endoscope 10. The display device 70 displays the image information acquired by the capsule endoscope 10 based on the image information received by the receiving device 30. For example, a portable-type storage medium (portable storage medium) 50 is used for the transmission of the image information between the receiving device 30 and the display device 70.

The capsule endoscope 10 has an imaging function and a wireless-transmission function. The capsule endoscope 10 is swallowed from a mouth of the subject 1 and introduced inside the subject 1, and successively acquires image information of a body cavity moving through the body cavity. Then, the capsule endoscope 10 wirelessly transmits the acquired image information to an outside of the body.

The receiving device 30 includes plural receiving antennas A1 to An, and receives the image information wirelessly transmitted from the capsule endoscope 10 via each of the receiving antennas A1 to An. The portable storage medium 50, which is a storage medium such as a CompactFlash®, is detachably attached to the receiving device 30, and the received image information is successively stored in the portable storage medium 50. Thus, the receiving device 30 stores the image information of the inside of the subject 1 acquired by the capsule endoscope 10 in the portable storage medium 50 in order of time.

Each of the receiving antennas A1 to An is formed, for example, as a loop antenna, and dispersed at a predetermined position on a body surface of the subject 1 as shown in FIG. 1. Specifically, the receiving antennas A1 to An are dispersed, for example, at positions corresponding to the pathway of the capsule endoscope 10 inside the subject 1. Alternatively, the receiving antennas A1 to An are dispersed at positions on a jacket to be worn by the subject 1. In this case, as the subject 1 wears the jacket, the receiving antennas A1 to An are arranged at the predetermined positions on the body surface of the subject 1 corresponding to the pathway of the capsule endoscope 10 inside the subject 1. Further, the number of the receiving antennas is not limited as long as one or more receiving antennas are arranged on the subject 1.

The display device 70 is realized by a general-purpose computer such as a workstation and a personal computer, and the portable storage medium 50 is detachably attached to the display device 70. The display device 70 reads image information stored in the portable storage medium 50, and displays images of the read image information on a display such as an LCD and an ELD. Further, the display device 70 writes information of the subject 1 into the portable storage medium 50 as needed. Further, the display device may output images onto other mediums via a printer or the like.

Figure 2:
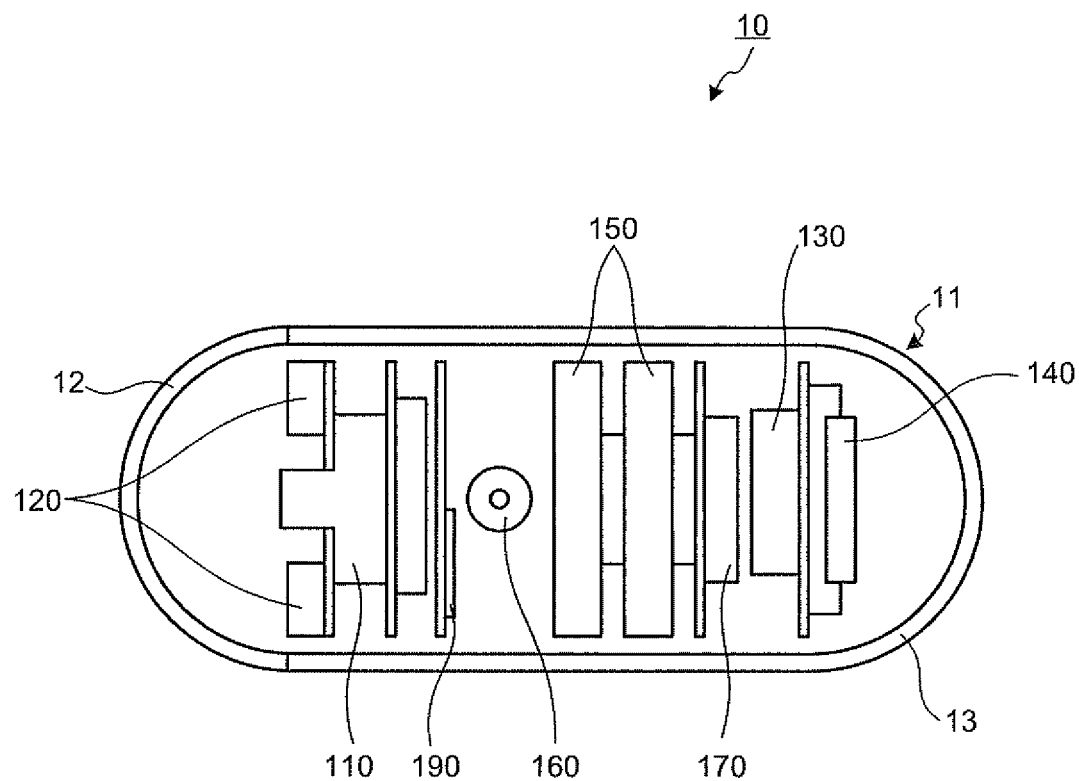
FIG. 2 is a schematic diagram of a configuration of the capsule endoscope according to the first embodiment.

The configuration of the capsule endoscope 10 according to the first embodiment is described. FIG. 2 is a schematic diagram of a configuration of the capsule endoscope 10. FIG. 3 is a block diagram of a functional configuration of the capsule endoscope 10. As shown in FIG. 3, the capsule endoscope 10 includes an imaging unit 110, an illuminating unit 120, a transmission processing unit 130, a power unit 150, a power switch 160, a power control unit 170, a ROM 180, a control unit 190 and the like. Further, as shown in FIG. 2, each of the units are contained inside a capsule-shaped casing 11. The imaging unit 110 acquires image information by capturing intracelomic images. The illuminating unit 120 emits illuminating light to the inside of the body cavity. The transmission processing unit 130 wirelessly transmits the image information acquired by the imaging unit 110 via a transmitting antenna 140. The power unit 150 supplies driving power for each unit forming the capsule endoscope 10. The power switch 160 switches supply/block of the driving power supplied by the power unit 150. The power control unit 170 controls the supply state of the driving power supplied by the power unit 150.

A casing 11 has a size which can be swallowed by a human. The casing 11 is formed with a hemispherical-shaped head cover 12 and a body cover 13 connected together. The head cover 12 is made of a transparent material, and works as an optical window. Specifically, in the casing 11, the imaging unit 110 and the illuminating unit 120 are arranged at opposing positions to the head cover 12. The illuminating light from the illuminating unit 120 transmits through the head cover 12 to an outside of the casing 11, and reflected light is introduced into the inside of the casing 11 through the head cover 12.

The imaging unit 110 is formed by an imaging device including image sensors such as a CCD and a CMOS, an imaging lens which forms incident light on the imaging device, and the like. The imaging unit 110 performs an imaging operation to capture images inside the subject 1 by outputting an analog signal corresponding to intensity of the incident light. Specifically, the imaging unit 110 performs the imaging operation at a supply timing of an imaging-unit-driving pulse from a timing generator 191 described later.

The illuminating unit 120 is formed, for example, by a light-emitting device such as an LED, a driving circuit for the light-emitting device, and the like. The illuminating unit 120 performs an illuminating operation to illuminate a portion captured by the imaging unit 110 by emitting illuminating light. Specifically, the illuminating unit 120 starts the illuminating operation at a supply timing of an illuminating-unit-driving pulse from the timing generator 191. The illuminating unit 120 emits illuminating light for light-emitting time corresponding to a pulse width of the supplied illuminating-unit-driving pulse to thereby emit the illuminating light by a light-emitting amount controlled by a light controller 194 described later.

The transmission processing unit 130 is formed by a transmission circuit which generates a wireless-transmission signal by performing a modulating process or the like on a transmission signal that is input from a signal processor 193 as needed, and the like.

The power switch 160 is a main switch of the capsule endoscope 10, and switches ON/OFF states by detecting an external input. The power switch 160 is formed, for example, by a reed switch, which switches ON/OFF states according to an external magnetic field. The power switch detects whether the magnet is close to or away from the reed switch as the external input, and outputs an ON signal or an OFF signal to the power control unit 170.

The power control unit 170 switches the supply/block states of the driving power supplied from the power unit 150 based on ON/OFF signals transmitted from the power unit 150. The power control unit 170 distributes the driving power supplied from the power unit 150 among the imaging unit 110, the illuminating unit 120, the transmission processing unit 130, the control unit 190, and the like. Specifically, each unit of the capsule endoscope 10 is connected with the power unit 150 via the power control unit 170 in such a manner that the supply state or the block state of electricity can be switched, so that the power unit 150 supplies the driving power for each unit under a control by the power control unit 170.

Specifically, the power control unit 170 controls a toggle of the power switch 160 according to the external input that is input to the power switch 160 so as to start the supply of driving power for each unit of the apparatus from the power unit 150 or block the supply. When a magnet is moved toward the power switch 160 and moved away from the power switch 160 as the external input, the state of the driving power from the power unit 150 is switched from the supply state to the block state or vice versa. The current state, the supply state or the block state, is maintained without the external input.

The power control unit 170 includes a mode-control counter 171. The mode-control counter 171 counts a number of times of switching the block state to the supply state of the driving power from the power unit 150 based on the ON/OFF signals from the power switch 160. For example, the mode-control counter 171 sets an initial value at "0", and increments the counted number every time the block state is switched to the supply state. The mode-control counter 171 outputs the updated counted number to the identification unit 195.

The ROM 180 stores therein various data required for operations of the capsule endoscope 10. The ROM 180 stores therein mode information 181, whereby the control content of the capsule endoscope 10 for each operation mode is set.

FIG. 4 is a diagram showing an example of an operation mode of the capsule endoscope 10 stored in the ROM 180 as the mode information 181 and a control content of the capsule endoscope 10 operating on the operation mode. In the example shown in FIG. 4, four types of operation modes identified as mode numbers "1" to "4" are set as the operation mode, and the control content is set for each of the operation modes. For example, the control content according to the operation mode which is identified as the mode number "1" is stored in a storage area whose initial address is an address "00" in the ROM 180 (record R1). Each operation mode has the control content, for example, corresponding to the portion where the capsule endoscope 10 passes inside the subject 1, in order of portions of passage. Specifically, the operation mode of the mode number "1" is an operation mode assuming a case where the capsule endoscope 10 passes through an esophagus. Since the capsule endoscope 10 moves through the esophagus at high speed, a high frame rate of 30 fps and compression of the acquired image information are assigned to the mode number "1". The operation mode of the mode number "12" is an operation mode assuming a case where the capsule endoscope passes through a stomach. In the stomach, since the capsule endoscope moves inside a large space, a relatively lower frame rate of 4 fps and non-compression of the acquired image information are assigned to the mode number "2". The operation mode of the mode number "3" is an operation mode assuming a case where the capsule endoscope passes through a small intestine. Since the capsule endoscope 10 moves through the small intestine at low speed, a low frame rate of 2 fps and non-compression of the acquired image information are assigned to the mode number "3". The operation mode of the mode number 411 is an operation mode assuming a case where the capsule endoscope passes through a large intestine. Since the capsule endoscope moves through the large intestine at even lower speed, an even lower frame rate of 2 fps and non-compression of the acquired image information are assigned to the mode number "4". Further, the control content may be set, for example, as a value of frame rate, a variable of flag information for compression/non-compression, or the like, or may be set as a control program which realizes the control content. Further, the operation mode may be the operation mode which specifies the frame rate, or one which specifies the compression/non-compression of the image information. Further, the operation mode may be the operation mode which specified a compression rate, one which specifies a light-control area described later, one which specifies a baseline luminance value, one which specifies a gain control value, or the like as needed.

The control unit 190 controls each unit of the capsule endoscope 10 to control the entire operation of the capsule endoscope 10. The control unit 190 includes a timing generator 191, a signal processor 193, a light controller 194, an identification unit 195, and a process determining unit 197.

The timing generator 191 generates driving timings for the imaging unit 110 and the illuminating unit 120 to control the imaging operation of the imaging unit 110, and the illuminating operation of the illuminating unit 120. For example, the timing generator 191 supplies an imaging-unit-driving pulse for the imaging unit 110 at predetermined intervals to control the imaging operation of the imaging unit 110, and supplies, right before the supply of the pulse to start the imaging operation, an illuminating-unit-driving pulse for the illuminating unit 120 to control the illuminating operation of the illuminating unit 120. Further, the timing generator 191 fluctuates a pulse width of the illuminating-unit-driving pulse according to light-emitting time input from the light controller 194 described later where a timing to start the operation is defined by a leading edge of the pulse and a timing to finish the operation is defined by a trailing edge of the pulse.

The signal processor 193 generates a transmission signal by performing processes needed for the image information acquired by the imaging unit 110. Specifically, the signal processor 193 performs an analog-signal processing such as a color balance adjustment and a gamma correction on an analog signal input from the imaging unit 110 to thereby convert the analog signal into a digital signal. Further, according to the acquired digital signal, the signal processor 193 generates the transmission signal to wirelessly transmit the acquired image information to an outside of the body. For example, when there is a signal frame having image information of a single image, the signal processor 193 attaches a vertical synchronizing signal to a head of the frame, and attaches a horizontal synchronizing signal to a head of constituent data of each line to thereby generate the transmission signal, and outputs the transmission signal to the transmission processing unit 130.

Figure 5:
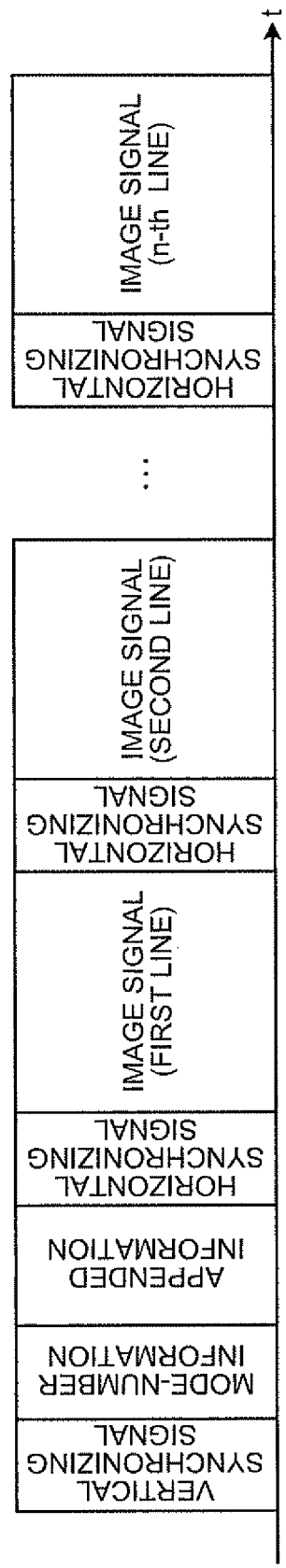
FIG. 5 is a diagram showing an example of a transmission signal.

FIG. 5 is a diagram showing an example of the transmission signal generated by the signal processor 193. As shown in FIG. 5, the transmission signal is formed with fields of the vertical synchronizing signal, mode-number information, and appended information, and with image signals having the horizontal synchronizing signal and corresponding to constituent data of each scan-line. The mode-number information is information input from the identification unit 195 described later, from which the operation mode can be identified. The appended information includes, for example, information such as a serial number of the capsule endoscope 10 and a white balance coefficient as needed. The transmission signal is input to the transmission processing unit 130 to be transmitted to the receiving device 30 arranged outside the body. The receiving device 30 receives the transmission signal, and then detects the head of the image based on the vertical synchronizing signal, and detects the head of the image signal of each line based on the horizontal synchronizing signal. The receiving device 30 processes each image signal, and acquires image information.

Further, the signal processor 193 calculates an average value of pixel values included in the predetermined light-control area of the acquired image information and outputs the average value to the light controller 194. For example, the signal processor 193 calculates the weighted average value of RGB values of each pixel forming the light-control area to obtain an average luminance value in the light-control area.

The light controller 194 performs a light control to control light-emitting amount of the illuminating light emitted from the illuminating unit 120. Specifically, the light controller 194 compares the average value input from the signal processor 193 to the baseline luminance value previously set as a threshold value, to determine the luminance of the light-control area in the acquired image information. As the baseline luminance value, a value with which an user can easily view a content of the image may be set. The light controller 194 calculates the light-emitting time of the illuminating unit 120 based on the result of comparison, and outputs the calculated light-emitting time to the timing generator 191. Thus, the light-emitting amount of the illuminating light on a following imaging operation is controlled based on the luminance in the light-control area of the acquired image information, whereby image quality of the captured image can be stably maintained. For example, when the luminance is high, the following light-emitting time of the illuminating unit 120 is set short whereas when the luminance is low, the following light-emitting time of the illuminating unit 120 is set long. Further, the control method of the light-emitting amount is not limited to the control of the light-emitting time. For example, the light-emitting amount may be controlled by adjusting a current value supplied for the light-emitting device forming the illuminating unit 120, or by changing the light-emitting luminance of the light-emitting device.

The identification unit 195 identifies the mode number based on the counter value that is counted by the mode-control counter 171, and outputs the mode number to the process determining unit 197. Further, the identification unit 195 outputs the identified mode number to the signal processor 193 as the mode-number information. Accordingly, the information of the operation mode on which the image information is captured is added to the transmission signal generated by the signal processor 193. Further, the identification unit 195 performs a control to initialize the counter value of the mode-control counter 171 at an initial value "0" as default, and a control to initialize the counter value to the initial value "0" when the counter value of the mode-control counter 171 is the maximum of the mode numbers (i.e., "4" in the example in FIG. 4).

The process determining unit 197 accesses, based on the mode number identified by the identification unit 195, storage area in the ROM 180 where the control content according to the operation mode of the mode number is stored. For example, when the mode number identified by the identification unit 195 is "1" shown in the record R1 in FIG. 4, the process determining unit 197 accesses the storage area whose head address is "00" to read out the control content. Further, the process determining unit 197 outputs a specified frame rate of 30 fps to the timing generator 191, whereby the process of the timing generator 191 is determined. Accordingly, the timing generator 191 supplied the imaging-unit-driving pulse for the imaging unit 110 at intervals of 1/30 seconds, and supplies, right before the supply of the imaging-unit-driving pulse, the illuminating-unit-driving pulse for the illuminating unit 120. Further, the timing generator 191 outputs a compression signal to the signal processor 193, whereby the process of the signal processor 193 is determined. Accordingly, the signal processor 193 performs a compression process on the image information acquired by the imaging unit 110.

Figure 6:
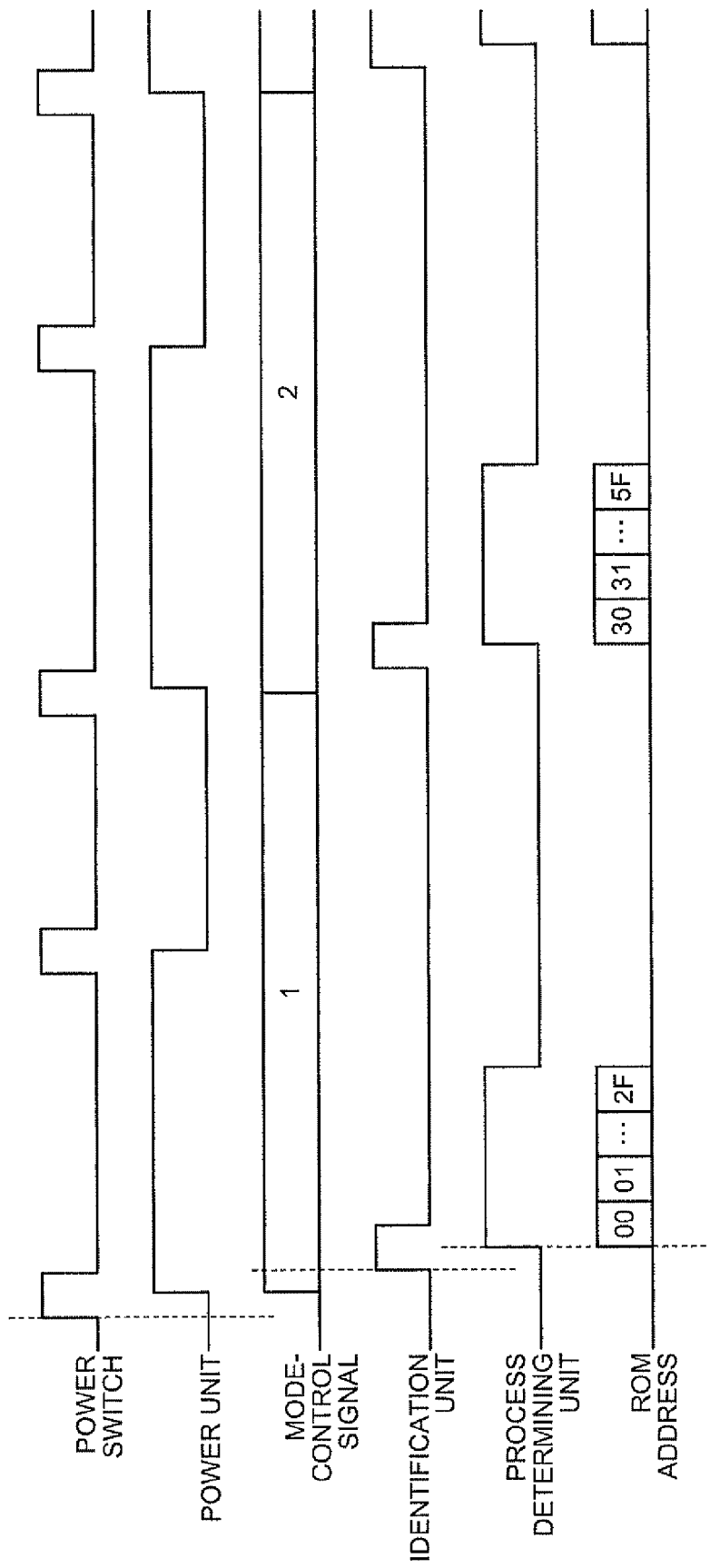
FIG. 6 is a timing chart according to a setting of the operation mode according to the first embodiment.

FIG. 6 shows a timing chart explaining the processes of the identification unit 195 and the process determining unit 197 according to the setting of the operation mode according to the first embodiment. As shown in FIG. 6, the power switch 160 first detects the external input and outputs the ON/OFF signals, and the power control unit 170 switches the supply/block states of the driving power from the power unit 150 according to the ON/OFF signals. The power control unit 170 maintains the supply state or the block state until the power switch 160 detects the external input.

When the driving power from the power unit 150 is switched from the block state to the supply state by the power control unit 170 according to the ON/OFF signals from the power switch 160, the mode-control counter 171 increments and updates the counter value. The mode-control counter outputs the counter value as a mode-control signal. For example, when the state is switched to the supply state for the first time, the initial value "0" is incremented, and "1" is output as the mode-control signal.

The identification unit 195 identifies the mode number of the operation mode to be set according to the mode-control signal, and outputs the mode number. For example, when the mode-control signal is "1", the identification unit 195 identifies the mode number as "1", and outputs "1".

The process determining unit 197 reads out the control content according to the operation mode of the mode number from the ROM 180 according to the mode number identified by the identification unit 195. For example, when the mode number identified by the identification unit 195 is "1", read addresses starts from "00" and "01" to "2F" successively, and the process determining unit 197 reads out the control content according to the corresponding operation mode from the mode information stored in the ROM 180. The process determining unit 197 determines the process according to the read control content. Thus, every time the driving power from the power unit 150 is switched from the block state to the supply state according to the detection of the external input, the operation mode is sequentially set and changed starting from the mode number "1".

Figure 7:
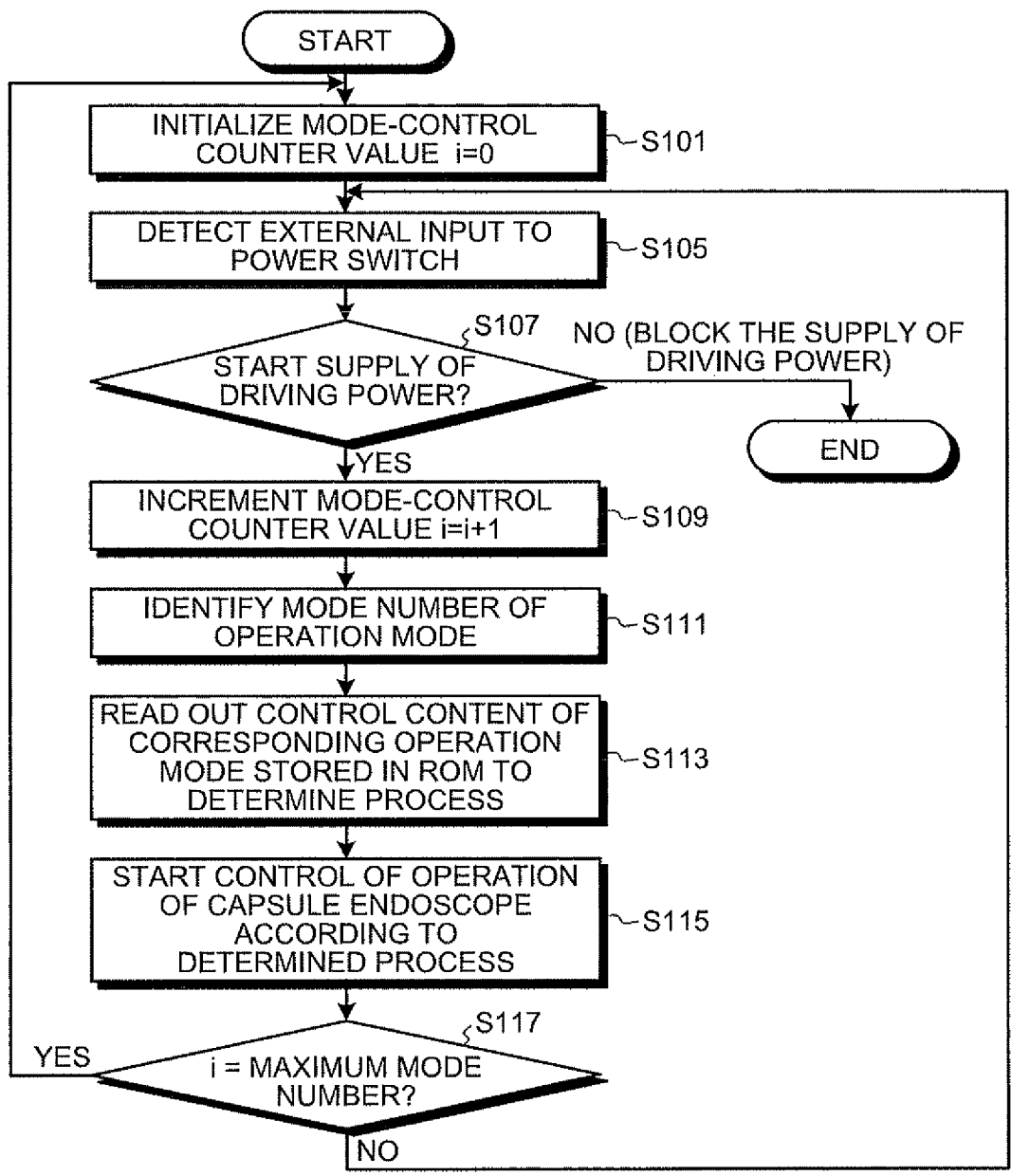
FIG. 7 is an operation flowchart of the capsule endoscope according to the first embodiment.

A procedure of the capsule endoscope 10 according to the first embodiment is described. FIG. 7 is an operation flowchart of the capsule endoscope 10 according to the setting of the operation mode. In the processes, the identification unit 195 performs a control to initialize the counter value of the mode-control counter 171 at the initial value "0" (Step S101). When the power switch 160 detects the external input (Step S105), the power control unit 170 switches the supply/block states of the driving power from the power unit 150. When the driving power is switched from the supply state to the block state so that the supply of the driving power is blocked (Step S107: No), the power is turned off as a reset procedure or the like of internal circuits is executed. On the other hand, when the driving power is switched from the block state to the supply state so that the supply of the driving power is started (Step S107: Yes), the mode-control counter 171 increments and updates the counter value, and outputs the counter value to the identification unit 195 as the mode-control signal (Step S109).

The identification unit 195 identifies the operation mode to be set based on the mode-control signal input from the mode-control counter 171 (Step S111). The process determining unit 197 reads out the control content of the corresponding operation mode according to the identified mode number from the ROM 180, and determines the process according to the read control content (Step S113). The control unit 190, which includes timing generator 191 and the signal processor 193, performs the process determined by the process determining unit 197, and starts controlling the operation of each unit of the apparatus (Step S115). Further, the identification unit 195 identifies the mode number, which is identified at Step S111. When the mode number identified at Step S111 is the maximum of the mode numbers (Step S117: Yes), the control unit 190 returns to Step S101 and performs a control to initialize the counter value of the mode-control counter 171 at the initial value "0". When the mode number identified at Step S111 is not the maximum of the mode numbers (Step S117: No), the control unit 190 returns to Step S105 and repeats the operations above.

Figure 8:
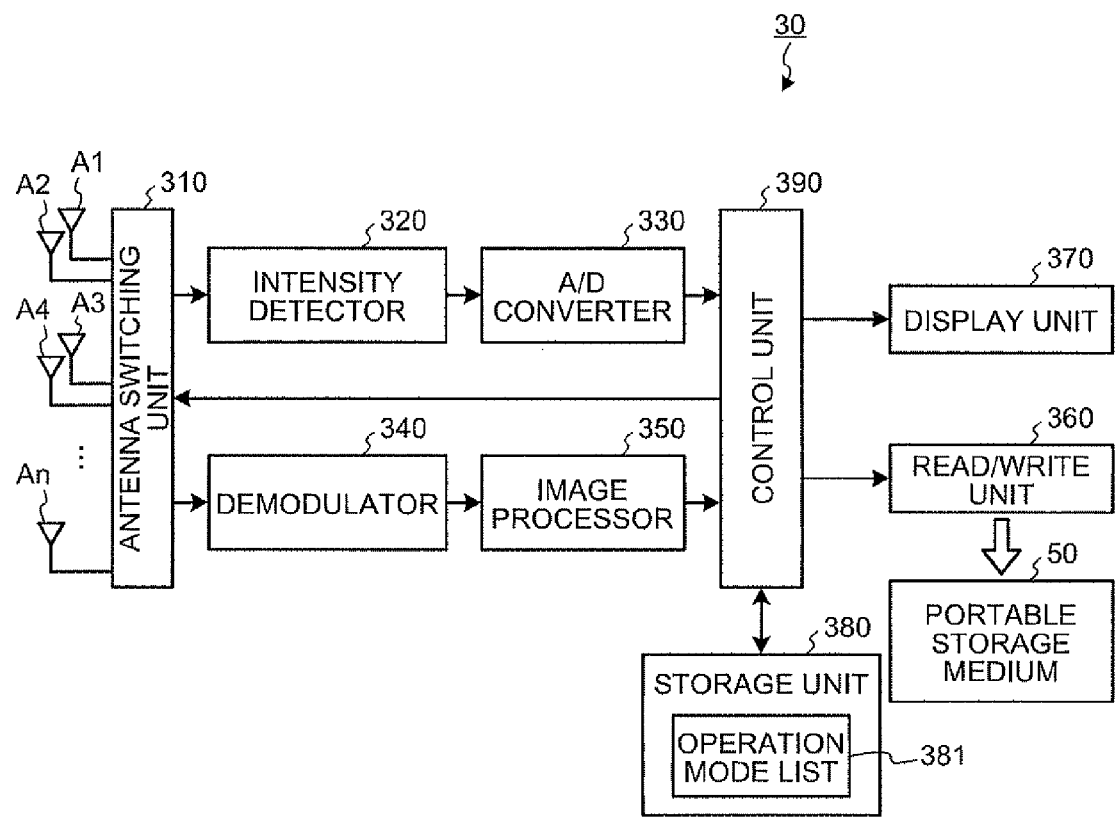
FIG. 8 is a block diagram of a functional configuration of a receiving device.

A configuration of the receiving device 30 which receives the image information wirelessly transmitted from the capsule endoscope 10 is described. FIG. 8 is a block diagram of a functional configuration of the receiving device 30. As shown in FIG. 8, the receiving device 30 includes antennas A1 to An, an antenna switching unit 310, an intensity detector 320, an A/D converter 330, a demodulator 340, an image processor 350, a read/write unit 360, a display unit 370, a storage unit 380, and a control unit 390.

The antenna switching unit 310 switches the receiving antennas to receive the wireless-transmission signal transmitted from the capsule endoscope 10 to one of the receiving antennas A1 to An. The antenna switching unit 310 is connected to the receiving antennas A1 to An via cables, respectively. The antenna switching unit 310 receives the wireless-transmission signal transmitted from the capsule endoscope 10 via the receiving antenna selected from the receiving antennas A1 to An by the control unit 390, and outputs the wireless-transmission signal to the demodulator 340. Further, the antenna switching unit 310 receives the wireless-transmission signal via each of the receiving antennas A1 to An, and outputs the wireless-transmission signal to the intensity detector 320.

The intensity detector 320 detects the reception intensity of the wireless-transmission signal which is received via the antenna switching unit 310 from the capsule endoscope 10, and outputs the detected reception intensity to the A/D converter 330. The A/D converter 330 performs an A/D conversion on the detection result of the reception intensity which is input from the intensity detector 320.

The demodulator 340 demodulates the wireless-transmission signal which is received via the antenna switching unit 310 from the capsule endoscope 10 to thereby demodulate the wireless-transmission signal into an image signal. The image signal corresponds to the transmission signal generated in the capsule endoscope 10. The image signal includes the image information acquired by the capsule endoscope 10, the vertical synchronizing signal included in each frame, the horizontal synchronizing signal included in each line of a frame, the mode-number information, and the appended information. The demodulator 340 outputs the demodulated image signal the image processor 350.

The image processor 350 performs a predetermined imaging process on the demodulated image signal, and converts the image signal into image data having a desired format, and outputs the image signal to the control unit 390.

The read/write unit 360 has the portable storage medium 50 detachably attached thereto. The read/write unit 360 sequentially stores the image information on which the image processing has been performed by the image processor 350 in the portable storage medium 50. The read/write unit 360 is realized by a reading-writing apparatus corresponding to a type of the portable storage medium 50.

The display unit 370 displays images of various screens containing the in-vivo images received from the capsule endoscope 10. The display unit 370 is realized by a compact LCD, an EL display, or the like.

The storage unit 380 is realized by IC memories, for example, a ROM or a RAM such as a flash memory, which can be overwritten. The storage unit 380 stores programs for the operation of the receiving device 30, programs for realizing the various functions of the receiving device 30, and data needed for executing the programs.

Further, the storage unit 380 stores an operation-mode list 381. The operation-mode list 381 is a data table storing a list of the operation modes of the capsule endoscope 10, where the control content of the capsule endoscope 10 is set for the corresponding operation mode for each mode number. In the first embodiment, the correspondence relation between the control content and mode numbers shown in FIG. 4 is set.

The control unit 390 controls the overall operation of the receiving device 30. The control unit 390, for example, instructs and transfers data to each unit forming the receiving device 30 based on the programs, data, and the like stored in the storage unit 380. For example, the control unit 390 selects one of the receiving antennas A1 to An which is the most suitable for receiving the wireless-transmission signal from the capsule endoscope 10. Specifically, the control unit 390 selects one of the receiving antennas A1 to An which has the highest reception intensity of the wireless-transmission signal from the capsule endoscope 10 based on the reception intensity input from the intensity detector 320 via the A/D converter 330. Then, the control unit 390 controls the switching operation of the antenna switching unit 310 to switch to the selected receiving antenna. Further, the control unit 390 controls the read/write unit 360 to sequentially store the image information processed by the image processor 350 in the portable storage medium 50, and displays the image information image information on the display unit 370. Further, on the displaying operation, the control unit 390 displays the information of the operation mode on which the image information is captured based on the mode-number information received with the image information being displayed. Specifically, the control unit 390 reads out the corresponding control content according to the operation-mode list stored in the storage unit 380, and displays the control content with the image information on screen.

According to the first embodiment described above, when the external input to the power switch 160 is detected, and the power control unit 170 switches to the supply state of the driving power from the power unit 150, the operation mode can be set according to the number of times of switching. Further, according to the control content of the set operation mode, the operation of each unit of the apparatus can be controlled. Thus, the operation mode can be changed and set based on the external input to the power switch 160 to switch the supply state of the driving power, whereby the setting of the operation mode can be realized with a simple configuration using the power switch conventionally used in the capsules-shaped endoscope 10. Further, the operation mode can be changed and set at any desired timing. In the first embodiment, the operation mode is set corresponding to the portion the capsule endoscope passes in order of portions of passage. Thus, for example, the operation mode is switched according to the time elapsed since the capsule endoscope 10 is introduced inside the subject 1 or the like, whereby the most suitable operation mode can be set and the image information can be acquired on the most suitable operation mode being set. Further, the control content of each operation mode is stored in the ROM 180, whereby the operation of the capsule endoscope 10 can be controlled according to the corresponding operation mode by reading out the control content according to the operation mode. Thus, the size of circuits can be maintained small compared with a case where the setting/change of the operation mode is realized by circuits. Further, the operation mode is changed and set every time the driving power is switched from the block state to the supply state, whereby the supply of power is securely blocked before the operation mode is changed and the power is turned off. Thus, advantageously, the operation mode can be set and changed after the internal circuit is reset.

Further, when the receiving device 30 displays the image information wirelessly transmitted from the capsule endoscope 10 on screen, the receiving device 30 can display the information of the operation mode on which the image information is captured. Thus, an observer can check the current operation mode of the capsule endoscope inside the subject 1 as needed when the observer inputs the external input to the power switch 160 to change and set the operation mode of the capsule endoscope 10.

Further, in the first embodiment, when the external input to the power switch 160 is detected, and the power control unit 170 switches the block state of the driving power from the power unit 150 to the supply state, the operation mode is set according to the number of times of switching. Alternatively, the operation mode may be set according to the number of time of switching when the supply state is switched to the block state.

Figure 9:
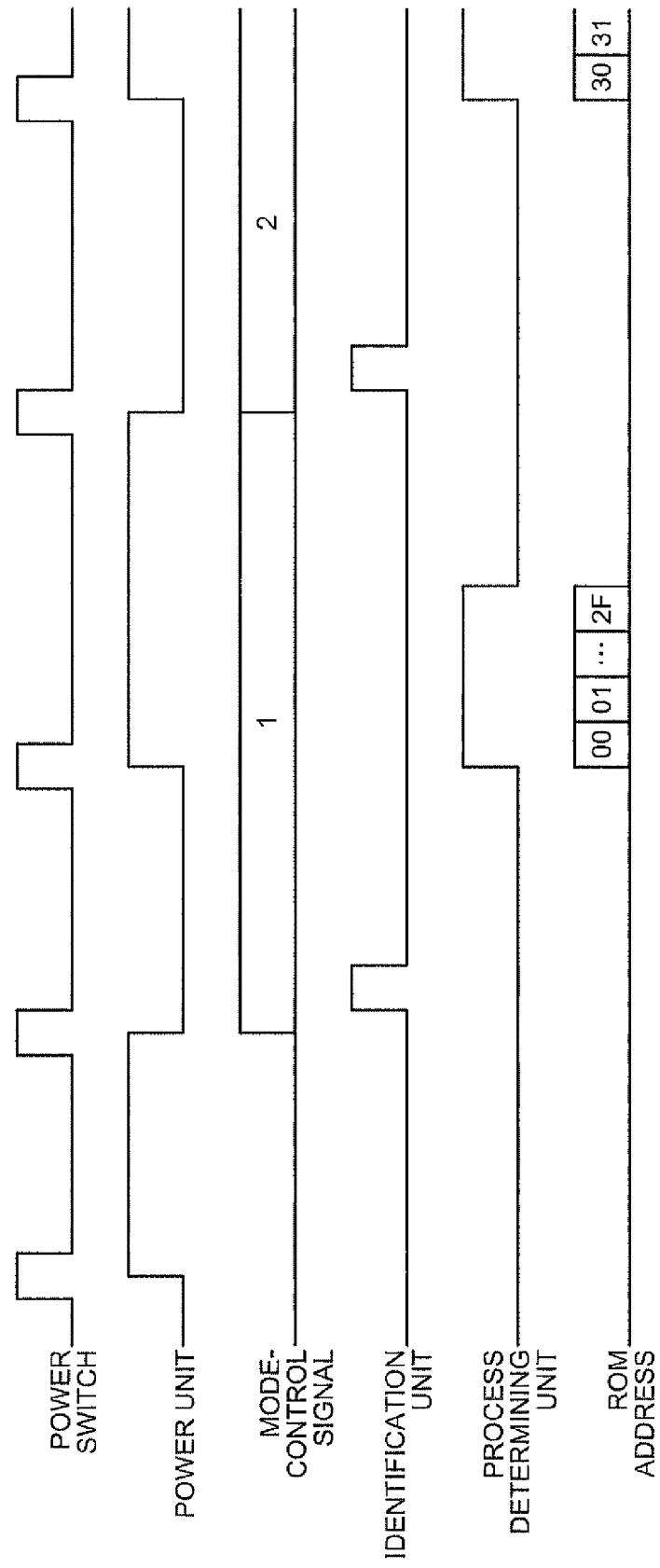
FIG. 9 is a timing chart according to a setting of an operation mode according to a variation.

FIG. 9 is a timing chart explaining the processes of the identification unit 195 and the process determining unit 197 according to a setting of the operation mode according to the present variation. As shown in FIG. 9, when the power switch 160 detects the external input and outputs the ON/OFF signals, the power control unit 170 switches the supply/block states of the driving power from the power unit 150 according to the ON/OFF signals. The power control unit 170 starts or blocks the supply of the driving power for each unit of the apparatus.

Further, when the power control unit 170 switches the supply state of the driving power from the power unit 150 to the block state according to the ON/OFF signals from the power switch 160, the mode-control counter 171 increments and updates the counter value. Then, the power control unit 170 outputs the counter value as the mode-control signal. For example, when the driving power is switched to the block state for the first time, the initial value "0" is incremented to be "1", and output as the mode-control signal.

Further, when the power control unit 170 switches the block state of the driving power from the power unit 150 to the supply state according to the ON/OFF signals from the power switch 160, the identification unit 195 identifies the mode number of the operation mode to be set based on the mode-control signal. The process determining unit 197 generates the read addresses according to the mode number identified by the identification unit 195, and reads out the control content according to the operation mode of the mode number from the ROM 180 to determine the process.

Figure 10:
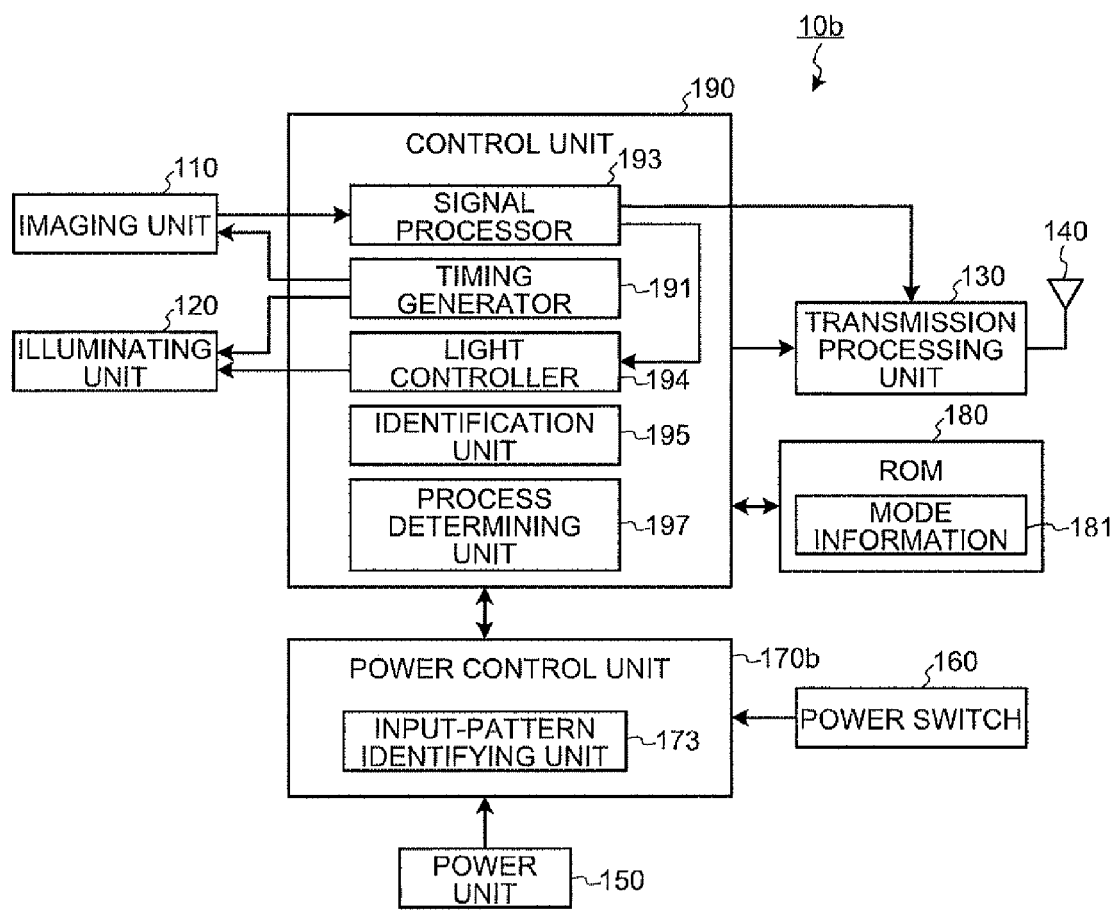
FIG. 10 is a block diagram of a functional configuration of a capsule endoscope according to a second embodiment.

A second embodiment is described. FIG. 10 is a block diagram of a functional configuration of a capsule endoscope 10*b* according to the second embodiment. Same numerals are attached to components which are identical with those in the first embodiment. As shown in FIG. 10, the capsule endoscope 10*b* includes the imaging unit 110, the illuminating unit 120, the transmission processing unit 130, the transmitting antenna 140, the power unit 150, the power switch 160, a power control unit 170*b*, the ROM 180, and the control unit 190.

In the second embodiment, the power control unit 170*b* includes an input-pattern identification unit 173 to identify an input pattern of the external input from the power switch 160, and outputs the mode number corresponding to the result of identification to the identification unit 195 as the mode-control signal. Specifically, correspondent relations between the input pattern of the external input and the mode number are previously defined, and the input-pattern identification unit 173 outputs the mode number corresponding to the identified input pattern.

Figure 11:
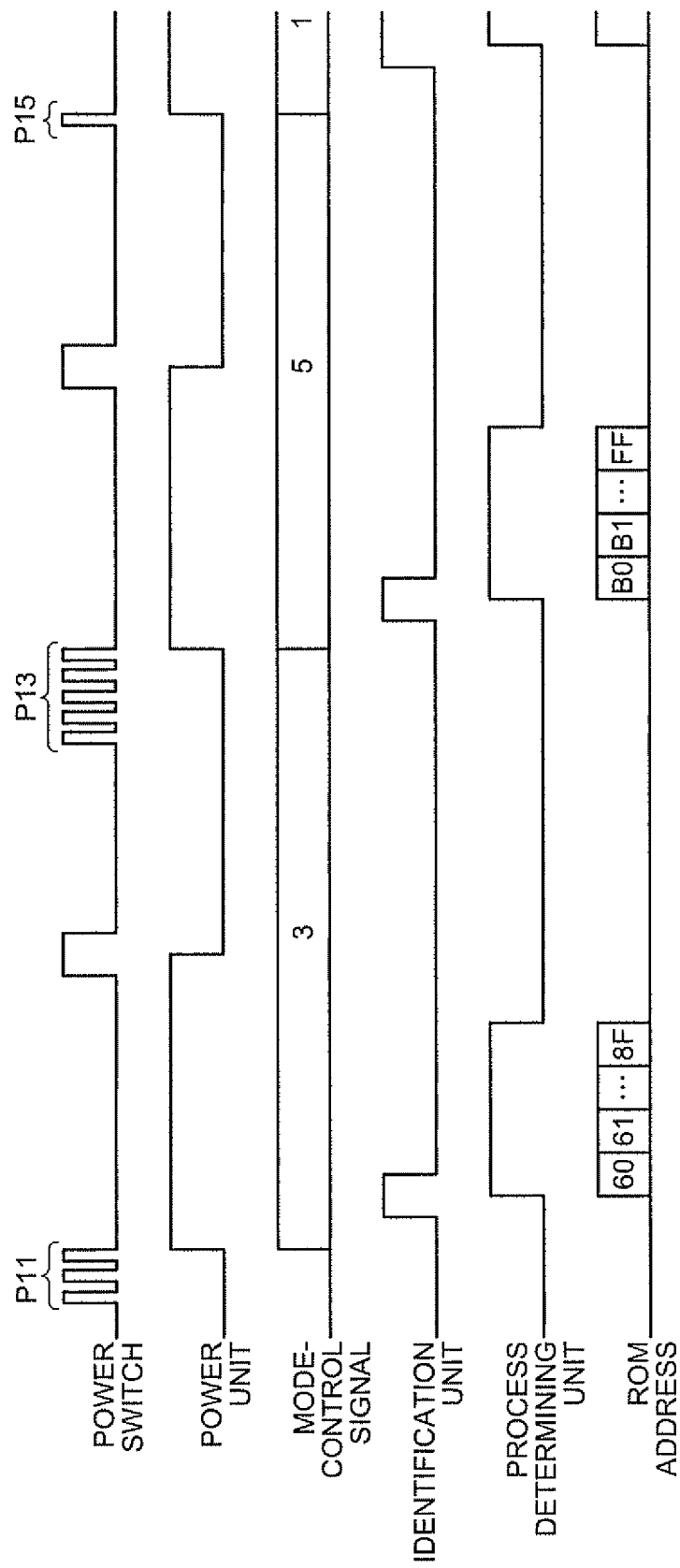
FIG. 11 is a timing chart according to a setting of an operation mode according to the second embodiment.

FIG. 11 is a timing chart explaining processes of the identification unit 195 and the process determining unit 197 according to a setting of the operation mode according to the second embodiment. As shown in FIG. 11, when the power switch 160 detects the external input and outputs the ON/OFF signals, the power control unit 170*b* switches the supply/block states of the driving power from the power unit 150 according to the ON/OFF signals. The power control unit 170*b* starts or blocks the supply of the driving power for each unit of the apparatus. The power control unit 170*b* maintains the supply state or the block state until the power switch 160 detects the external input.

When the power control unit 170*b* switches the block state of the driving power from the power unit 150 to the supply state according to the ON/OFF signals from the power switch 160, the input-pattern identification unit 173 identifies the input pattern of the external input. For example, in the example shown in FIG. 11, an input pattern P11 of the external input is previously associated with the mode number "3", and the mode number "3" is output as the mode-control signal. Further, an input pattern P13 of the external input is previously associated with the mode number "5", and the mode number "5" is output as the mode-control signal. Further, an input pattern P15 of the external input is previously associated with the mode number "1", and the mode number "1" is output as the mode-control signal.

The identification unit 195 identifies the mode number of the operation mode to be set based on the mode-control signal. The process determining unit 197 reads out the control content according to the operation mode of the mode number according to the mode number identified by the identification unit 195 from the ROM 180 to determine the process. Thus, the operation mode is changed and set suitably for the input pattern of the external input every time the external input is detected and the driving power from the power unit 150 is switched from the block state to the supply state.

Figure 12:
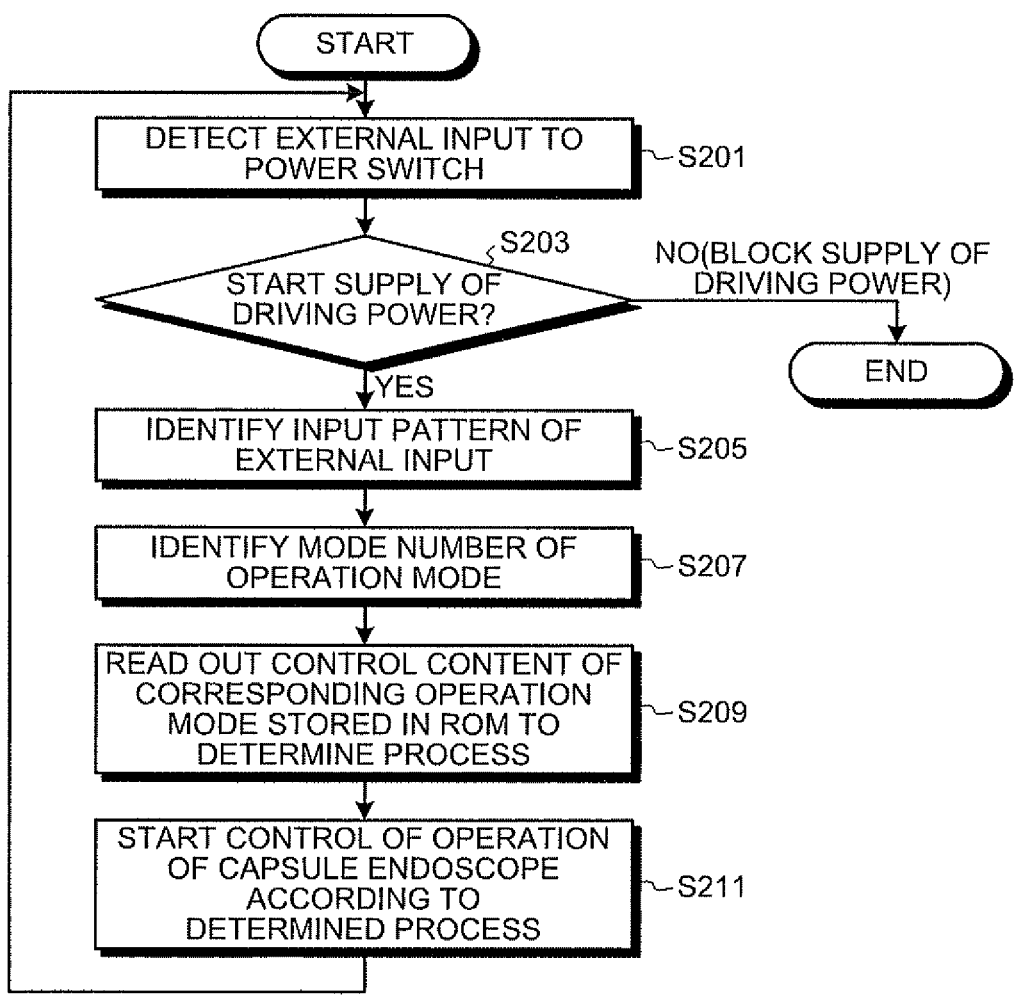
FIG. 12 is an operation flowchart of the capsule endoscope according to the second embodiment.

An operation procedure of the capsule endoscope 10*b* according to the second embodiment is described. FIG. 12 is an operation flowchart of the capsule endoscope 10*b* according to the setting of the operation mode. AS shown in FIG. 12, when the power switch 160 detects the external input (Step S201), the power control unit 170*b* switches the supply/block states of the driving power from the power unit 150. When the supply state is switched to the block state to block the supply of the driving power (Step S203: No), the power is turned off as the reset process or the like is performed on the internal circuit. On the other hand, when the block state is switched to the supply state to start the supply of the driving power (Step S203: Yes), the input-pattern identification unit 173 identifies the input pattern of the external input. Then, the input-pattern identification unit 173 outputs the mode number corresponding to the result of identification to the identification unit 195 as the mode-control signal (Step S205).

The identification unit 195 identifies the mode number of the operation mode to be set based on the mode-control signal which is input from the input-pattern identification unit 173 (Step S207). The process determining unit 197 reads out the control content of the corresponding operation mode according to the identifies mode number from the ROM 180, and determines the process according to the read control content (Step S209). The control unit 190, which includes the timing generator 191 and the signal processor 193, performs the process determined by the process determining unit 197, and starts the control of the operation of each unit of the apparatus (Step S211). Then, the control unit 190 returns to Step S201 and repeats the operations above.

The image information acquired by the capsule endoscope configured as above is wirelessly transmitted to the receiving device similarly to the first embodiment. The receiving device 30 sequentially stores the received image information in the portable storage medium 50, and displays the image information on the display unit 370. Similarly to the first embodiment, the receiving device 30 may display the information of the operation mode on which the image information is captured on screen based on the mode-number information which is received with the image information to be displayed.

According to the second embodiment described above, when the external input to the power switch 160 is detected, and the power control unit 170b switches the driving power from the power unit 150 to the supply state, the operation mode can be set corresponding to the input pattern of the external input. Further, according to the control content of the operation mode being set, the operation of each unit of the apparatus can be controlled. Thus, the operation mode can be changed and set according to the external input to the power switch 160 to switch the supply state of the driving power, whereby the advantage is realized similarly to the first embodiment. Further, the operation modes can be set at any timing, whereby the most suitable operation mode can be set at a desired timing, and the image information can be acquired on the most suitable operation mode being set.

Further, in the second embodiment, when the external input to the power switch 160 is detected, and the power control unit 170b switches the block state of the driving power from the power unit 150 to the supply state, the operation mode is set corresponding to the input pattern of the detected external input. Alternatively, the operation mode may be set corresponding to the input pattern of the detected external input when the supply state is switched to the block state.

Figure 13:
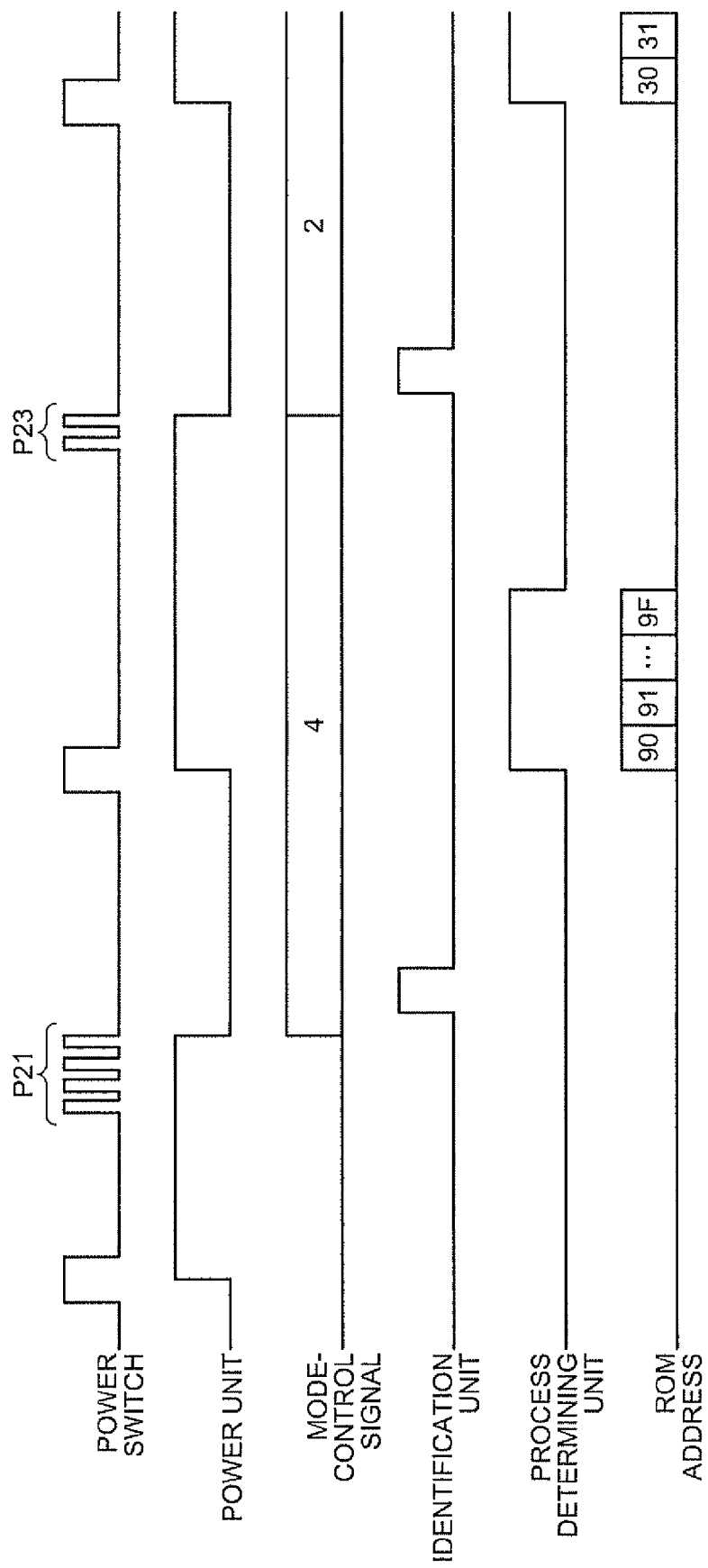
FIG. 13 is a timing chart according to a setting of an operation mode according to a variation.

FIG. 13 is a timing chart explaining the processes of the identification unit 195 and the process determining unit 197 according to a setting of the operation mode according to the present variation. As shown in FIG. 13, when the power switch 160 detects the external input and outputs the ON/OFF signals, the power control unit 170b switches the supply/block states of the driving power from the power unit 150 according to the ON/OFF signals. Thus, the power control unit 170b starts or blocks the supply of the driving power for each unit of the apparatus.

Further, when the power control unit 170b switches the supply state of the driving power from the power unit 150 to the block state according to the ON/OFF signals from the power switch 160, the input-pattern identification unit 173 identifies the input pattern of the external input. For example, in the example shown in FIG. 13, an input pattern P21 of the external input is previously associated with the mode number "4", and the mode number "4" is output as the mode-control signal. Further, an input pattern P23 of the external input is previously associated with the mode number "2", and the mode number "2" is output as the mode-control signal.

Further, when the power control unit 170b switches the block state of the driving power from the power unit 150 to the supply state according to the ON/OFF signals from the power switch 160, the identification unit 195 identifies the mode number of the operation mode to be set based on the mode-control signal, and outputs the mode number. The process determining unit 197 reads out the control content according to the operation mode of the mode number from the ROM 180 based on the mode number identified by the identification unit 195, and determines the process.

Figure 14:
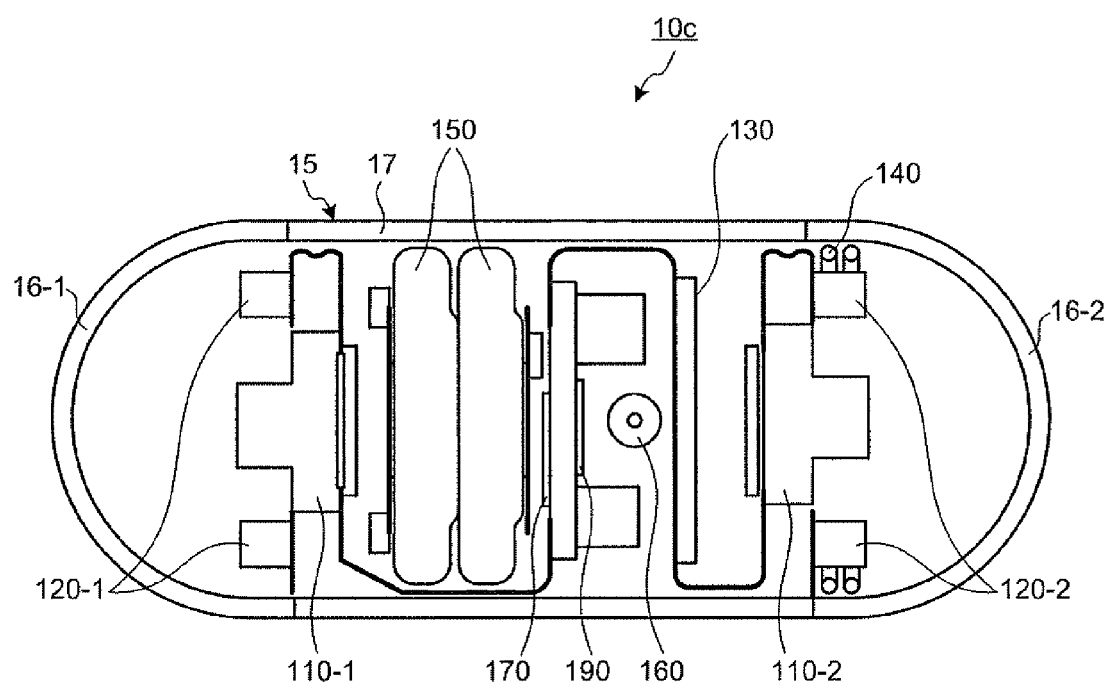
FIG. 14 is an overall schematic diagram of a configuration of a capsule endoscope according to a variation.

Further, in each of the embodiments above, the capsule endoscope having a pair of the imaging unit and the illuminating unit is described. The capsule endoscope may have two or more pairs of the imaging unit and the illuminating unit. FIG. 14 is a schematic diagram of a configuration of a capsule endoscope 10c having two pairs of the imaging unit and the illuminating unit. Same numerals are attached to components which are identical with those in the first embodiment.

The capsule endoscope 10c has the imaging unit and the illuminating unit at both ends, respectively. The capsule endoscope 10c can capture the image information in both forward and backward directions of movement, respectively. Specifically, as shown in FIG. 14, the capsule endoscope 10c includes the imaging units 110-1, 110-2, the illuminating units 120-1, 120-2, the transmission processing unit 130, the transmitting antenna 140, the power unit 150, the power switch 160, the power control unit 170, the control unit 190, and the like. Each of the units is contained inside the capsule-shaped casing 15.

The casing 15 is formed with hemispherical-shaped head covers 16-1, 16-2, and a cylindrical body cover 17 connected together. Further, the head covers 16-1, 16-2 are made of a transparent material, and work as optical windows. Specifically, the illuminating light from the illuminating unit 120-1 which is arranged at an opposing position to the head cover 16-1 in the casing 15 transmits through the head cover 16-1 to an outside of the casing 15, and reflected light is introduced into the casing 15 through the head cover 16-1. Similarly, the illuminating light from the illuminating unit 120-2 which is arranged at an opposing position to the head cover 16-2 in the casing 15 transmits through the head cover 16-2 to the outside of the casing 15, and reflected light is introduced into the casing 15 through the head cover 16-2.

When the present invention is applied to the capsule endoscope having two pairs of the imaging unit and the illuminating unit as described above, the operation modes may be set as follows. For example, the operation mode may be set for both of the imaging units 110-1, 110-2 to perform the imaging operation, and for both of the illuminating units 120-1, 120-2 to perform the illuminating operation so that the image information in both forward and backward directions of movement can be captured. Further, the operation mode may be set for either of the imaging units 110-1, 110-2 to perform the imaging operation, and for either of the illuminating units 120-1, 120-2 so that the image information in either forward or backward direction of movement can be captured.

According to the in-vivo image acquiring apparatus and the in-vivo image acquiring system according to the embodiments, the operation mode of the in-vivo image acquiring apparatus can be set based on the external input to the switching unit which switches the supply state of the driving power for each unit forming the in-vivo image acquiring apparatus. Further, the operation of each unit of the apparatus can be controlled according to the operation mode being set. Thus, the operation mode can be set based on the external input to switch the supply state of the driving power, whereby the setting of the operation mode can be realized with a simple configuration, and the setting of the operation mode can be performed at any desired timing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo image acquiring apparatus, introduced inside a subject, for capturing an inside of the subject, and outputting acquired image information to an outside, the in-vivo image acquiring apparatus comprising:
    an imaging unit that captures the inside of the subject;
    a transmission processing unit that performs a process that wirelessly transmits the image information captured by the imaging unit;
    a power supplying unit;
    a switching unit that detects an external input instructing start or stop of supply of driving power and switches a supply state of the driving power supplied by the power supplying unit based on the external input;
    a mode setting unit that sets an operation mode of the in-vivo image acquiring apparatus to one of a plurality of operation modes of the in-vivo image acquiring apparatus based on how many times the external input has been input to the switching unit; and
    a control unit that controls an operation of the imaging unit, the transmission processing unit, the power supplying unit, the switching unit and the mode setting unit of the in-vivo image acquiring apparatus according to the operation mode set by the mode setting unit,
    wherein the power supplying unit supplies the driving power for the imaging unit, the transmission processing unit, the control unit, the switching unit and the mode setting unit of the in-vivo image acquiring apparatus.

2. The in-vivo image acquiring apparatus according to claim 1, comprising
    a storage unit that stores a control content of the imaging unit, the transmission processing unit, the power supplying unit, the switching unit and the mode setting unit of the in-vivo image acquiring apparatus for each of the plurality of operation modes, wherein
    the control unit reads out the control content of the imaging unit, the transmission processing unit, the power supplying unit, the switching unit and the mode setting unit of the in-vivo image acquiring apparatus corresponding to the operation mode set by the mode setting unit from the storage unit, and controls the operation of the imaging unit, the transmission processing unit, the power supplying unit, the switching unit and the mode setting unit of the in-vivo image acquiring apparatus according to the read control content.

3. The in-vivo image acquiring apparatus according to claim 1, wherein
    the transmission processing unit performs a process that wirelessly transmits, along with image information captured by the imaging unit, information on the operation mode in which the image information has been captured.

4. The in-vivo image acquiring apparatus according to claim 1, wherein each of the plurality of operation modes specifies, with respect to the image information captured by the imaging unit, at least one of a frame rate and whether or not compression is to be performed.

5. An in-vivo image acquiring system, comprising:
    an in-vivo image acquiring apparatus, introduced inside a subject, for capturing an inside of the subject, and outputting acquired image information to an outside, the in-vivo image acquiring apparatus comprising an imaging unit that captures the inside of the subject, a transmission processing unit that performs a process that wirelessly transmits the image information captured by the imaging unit, a power supplying unit, a switching unit that detects an external input instructing start or stop of supply of driving power and switches a supply state of the driving power supplied by the power supplying unit based on the external input, a mode setting unit that sets an operation mode of the in-vivo image acquiring apparatus to one of a plurality of operation modes of the in-vivo image acquiring apparatus based on how many times the external input has been input to the switching unit, and a control unit that controls an operation of the imaging unit, the transmission processing unit, the power supplying unit, the switching unit and the mode setting unit of the in-vivo image acquiring apparatus according to the operation mode set by the mode setting unit, wherein the power supplying unit supplies the driving power for the imaging unit, the transmission processing unit, the control unit, the switching unit and the mode setting unit of the in-vivo image acquiring apparatus;
    a receiving unit, arranged outside of the subject, for receiving image information which is wirelessly transmitted from the in-vivo image acquiring apparatus information on the operation mode in which the image information has been captured; and
    a display processing unit which performs a process that displays the image information received by the receiving unit and the received operation-mode information on a display unit.

6. The in-vivo image acquiring apparatus according to claim 5, wherein each of the plurality of operation modes specifies, with respect to the image information captured by the imaging unit, at least one of a frame rate and whether or not compression is to be performed.

7. An in-vivo image acquiring apparatus that is introduced inside a subject, captures image information of an inside of the subject, and transmits the captured image information to an outside, the in-vivo image acquiring apparatus comprising:
    an imaging unit configured to operate in a plurality of operation modes having different image capturing conditions from one another;
    a transmission processing unit that performs a process that wirelessly transmits the image information captured by the imaging unit;
    a power supplying unit that supplies driving power;
    a power switch that generates a trigger pulse for switching between a supply state and a block state of the driving power supplied by the power supplying unit in response to an external input;
    a power control unit that cyclically repeats the supply state and the block state in response to the trigger pulse generated by the power switch;

a mode information storage unit that stores therein control contents corresponding to a plurality of operation modes;

a mode control counter that increments a counter to set a subsequent operation mode when the block state is switched to the supply state by the power control unit;

a control unit that controls operations of the imaging unit, the transmission processing unit, the power supplying unit, the power switch, the power control unit, the mode information storage unit, and the mode control counter of the in-vivo image acquiring apparatus according to the control contents stored in the mode information storage unit and the subsequent operation mode set by the mode control counter, wherein the power supplying unit supplies the driving power for the imaging unit, the transmission processing unit, the power supplying unit, the power switch, the power control unit, the mode information storage unit, and the mode control counter of the in-vivo image acquiring apparatus.

8. The in-vivo image acquiring apparatus according to claim 7, wherein the transmission processing unit performs a process that wirelessly transmits, along with image information captured by the imaging unit, information on the operation mode in which the image information has been captured.

9. The in-vivo image acquiring apparatus according to claim 7, wherein each of the plurality of operation modes specifies, with respect to the image information captured by the imaging unit, at least one of a frame rate and whether or not compression is to be performed.

* * * * *